United States Patent [19]

Lesher

[11] 4,118,557

[45] Oct. 3, 1978

[54] CYCLIC ALKYLIDENYL N-(LOWER-ALKYL)-3-(PYRIDINYL-)ANILINOMETHYLENEMALONATES

[75] Inventor: George Y. Lesher, Schodack, N.Y.

[73] Assignee: Sterling Drug Inc., New York, N.Y.

[21] Appl. No.: 819,693

[22] Filed: Jul. 28, 1977

Related U.S. Application Data

[62] Division of Ser. No. 675,607, Apr. 9, 1976, abandoned.

[51] Int. Cl.$^2$ .................. C07D 405/12; C07D 319/06
[52] U.S. Cl. ............................... 542/420; 260/343.5; 542/423; 260/297 R; 260/340.6
[58] Field of Search ................................ 542/420, 423

[56] References Cited

U.S. PATENT DOCUMENTS 3,563,981  2/1971  Lesher et al. ..................... 542/420

FOREIGN PATENT DOCUMENTS 45-33,887  10/1970  Japan ..................... 542/423

*Primary Examiner*—Allen B. Curtis
*Attorney, Agent, or Firm*—Robert K. Bair; B. Woodrow Wyatt

[57] ABSTRACT

Cyclic alkylidenyl N-(lower-alkyl)-3-PY-anilinomethylenemalonates (I), where PY is 4- or 3-pyridinyl or 4- or 3-pyridinyl having one or two lower-alkyl substituents, are prepared by reacting cyclic alkylidenyl (lower-alkoxy)methylenemalonate (II) with N-(lower-alkyl)-3-PY-aniline (III). Also, I is heated with polyphosphoric acid to produce 1-(lower-alkyl)-1,4-dihydro-4-oxo-7-PY-3-quinolinecarboxylic acid, known antibacterial agents. The N-(lower-alkyl)-3-PY-anilines are produced by reducing the corresponding N-(3-PY-phenyl)-(lower-alkanamides).

4 Claims, No Drawings

CYCLIC ALKYLIDENYL N-(LOWER-ALKYL)-3-(PYRIDINYL)ANILINOMETHYLENEMALONATES

CROSS-REFERENCE TO RELATED APPLICATIONS

This application is a division of copending Application Ser. No. 675,607, filed Apr. 9, 1976, now abandoned.

BACKGROUND OF THE INVENTION (a) Field of the Invention

This invention relates to cyclic alkylidenyl anilinomethylenemalonates, to a process for their preparation and to a process for converting them to known 3-quinolinecarboxylic acids useful as antibacterial agents.

(b) Description of the Prior Art

The term "pyridyl" used in the following presentation of the prior art has the same meaning as "pyridinyl", the preferred term now used in Chemical Abstracts and used hereinbelow in describing the instant invention.

The Lesher and Carabateas U.S. Pat. No. 3,753,993, issued Aug. 21, 1973, and U.S. Pat. No. 3,907,808, issued Sept. 23, 1975, show the preparation of 1,4-dihydro-1-(lower-alkyl)-4-oxo-7-(pyridyl)-3-quinolinecarboxylic acids, antibacterial agents, by reacting the corresponding 1,4-dihydro-4-oxo-7-(pyridyl)-3-quinolinecarboxylic acid or lower-alkyl ester with an alkylating agent, e.g., lower-alkyl halide, sulfate or sulfonate. These patents also show the preparation of the intermediate 1,4-dihydro-4-oxo-7-(pyridyl)-3-quinolinecarboxylic acids and lower-alkyl esters by reacting di-(lower-alkyl) ethoxymethylenemalonate with a 3-(pyridyl)aniline. Also shown are the preparations of the intermediate 3-(pyridyl)anilines, e.g., 4-(3-aminophenyl)-pyridine [same as 3-(4-pyridinyl)aniline] by reducing the corresponding 4-(3-nitrophenyl)pyridine and 4-(3-aminophenyl)-2-ethylpyridine by catalytically hydrogenating 2-chloro-6-ethyl-4-(3-nitrophenyl)pyridine.

The Lesher U.S. Pat. No. 3,563,981, issued Feb. 16, 1971, shows the preparation of various cyclic alkylidenyl Ar-aminomethylenemalonates, where Ar is an aromatic radical having one or two aromatic rings which can be benzenoid or 5- or 6-membered heteroaromatic, by reacting the appropriate aromatic amine with a mixture of a trialkyl orthoformate or trialkyl orthoacetate and a cyclic alkylidenyl malonate. Cyclic alkylidenyl anilinomethylenemalonates derived from anilines are converted by heating to 4-hydroxyquinolines having no substituent in the 3-position. This patent also shows that cyclic isopropylidenyl N-(lower-alkyl)anilinomethylenemalonates derived from N-(lower-alkyl)anilines did not undergo cyclization.

The Kohjin Co. Ltd. Japanese Provisional Patent Publication No. 50-100064/75, published Aug. 8, 1975 and based on Application No. 49-6071/74, filed Jan. 11, 1974, discloses that 6-ethylamino-2-picoline can be prepared by reducing 6-acetamido-2-picoline with lithium aluminum hydride. No experimental details are given for preparing 6-ethylamino-2-picoline, but it appears that the reduction of 6-acetamido-2-picoline with lithium aluminum hydride most likely would produce a mixture of the final product, some starting material, and probably one or more ring-hydrogenated by-products.

DETAILED DESCRIPTION INCLUSIVE OF PREFERRED EMBODIMENTS

In a composition aspect the invention resides in the compounds having formula I

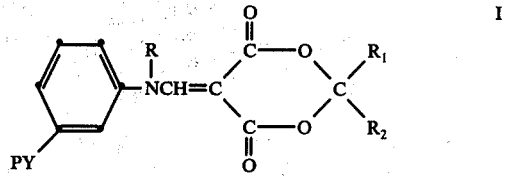

where PY is 4- or 3-pyridinyl or 4- or 3-pyridinyl having one or two lower-alkyl substituents, R is lower-alkyl, and $R_1$ and $R_2$ are each lower-alkyl. Preferred embodiments of I are the compounds where R is ethyl, $R_1$ and $R_2$ are each methyl and PY is 4-pyridinyl, 3-pyridinyl, 2-methyl-4-pyridinyl, 2-methyl-5-pyridinyl and 2,6-dimethyl-4-pyridinyl. The compounds of formula I are useful as intermediates in the preparation of 1-(lower-alkyl)-1,4-dihydro-4-oxo-7-PY-3-quinolinecarboxylic acids, which are useful as anti-bacterial agents.

In a process aspect the invention resides in the process of producing cyclic alkylidenyl N-(lower-alkyl)-3-PY-anilinomethylenemalonate having formula I given above which comprises reacting cyclic alkylidenyl (lower-alkoxy)methylenemalonate having formula II

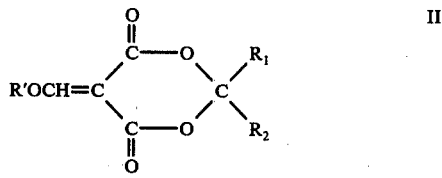

with N-(lower-alkyl)-3-PY-aniline (III) where $R_1$, $R_2$ and PY each has the meaning given hereinabove for I and R' is lower-alkyl, preferably methyl.

In another process aspect the invention resides in the process of heating cyclic alkylidenyl N-(lower-alkyl)-3-PY-anilinomethylenemalonate having formula I with polyphosphoric acid to produce 1-(lower-alkyl)-1,4-dihydro-4-oxo-7-PY-3-quinolinecarboxylic acid (V).

In another composition aspect the invention resides in the compounds having formula IV

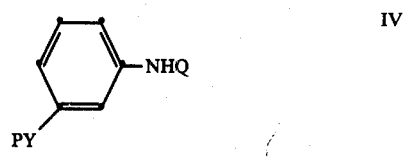

where PY is defined as above for I and Q is lower-alkanoyl or lower-alkyl, preferably acetyl or ethyl, respectively. These compounds are useful in the preparation of the compounds having formula I.

In another process aspect the invention resides in the process of producing N-(lower-alkyl)-3-PY-aniline (IV, Q = lower-alkyl) which comprises reacting N-(3-PY-phenyl)-(lower-alkanamide) (IV, Q = lower-alkanoyl) with a reducing agent capable of reducing lower-alkanoylamino (same as lower-alkanamido) to lower-alkylamino, said reducing agent preferably being diborane.

The term "lower-alkyl" as used herein, e.g., as the meaning for R, R', R$_1$, R$_2$ in I, II or III or as a substituent for PY in the compounds designated above as I, II or IV, means alkyl radicals having from one to six carbon atoms which can be arranged as straight or branched chains, illustrated by methyl, ethyl, n-propyl, isopropyl, n-butyl, sec-butyl, tert-butyl, isobutyl, n-amyl, n-hexyl, and the like.

The term "lower-alkanoyl", as used herein, e.g., as one of the meanings for Q in formula IV, means alkanoyl radicals having from one to six carbon atoms, including the straight- and branch-chained radicals, illustrated by formyl, acetyl, propionyl (n-propanoyl), butyryl (n-butanoyl), isobutyryl (2-methyl-n-propanoyl), caproyl (n-hexanoyl), and the like.

Illustrative of PY in the compounds of I, III, IV or V where PY is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds designated as I and III or those designated as IV where Q is lower-alkyl are useful both in the free base form and in the form of acid-addition salts, and, both forms are within the purview of the invention. The acid-addition salts are simply a more convenient form for use; and in practice, use of the salt form inherently amounts to use of the base form. Appropriately acceptable salts within the scope of the invention are preferably those derived from acids used to prepare medicinally acceptable salts, such acids derived from mineral acids such as phosphoric acid, hydrochloric acid, hydrobromic acid, sulfamic acid and sulfuric acid; and organic acids such as methanesulfonic acid, acetic acid, citric acid, lactic acid, tartaric acid, ethanesulfonic acid, benzenesulfonic acid, p-toluenesulfonic acid, cyclohexylsulfamic acid, quinic acid, and the like, giving the phosphate, hydrochloride, hydrobromide, sulfamate, sulfate, methanesulfonate, acetate, citrate, lactate, tartrate, ethanesulfonate, benzenesulfonate, p-toluenesulfonate, cyclohexylsulfamate and quinate, respectively.

The acid-addition salts are prepared preferably by reacting the free base and acid in an organic solvent, e.g., ethanol, acetone, etc., in which the salt separates directly or can be obtained by concentration of the solution.

The molecular structures of said composition aspects of the invention were assigned on the basis of evidence provided by infrared, ultraviolet and nuclear magnetic resonance and mass spectra, by chromatographic mobilities, and by the correspondence of calculated and found values for the elementary analysis for representative examples.

The manner of making and using the instant invention will now be generally described so as to enable a person skilled in the art of organic chemistry to make and use the same, as follows:

The preparation of the cyclic alkylidenyl N-(lower-alkyl)-3-PY-anilinomethylenemalonates of formula I is carried out by reacting cyclic alkylidenyl (lower-alkoxy)-methylenemalonate having formula II, where PY has the meaning given above for formula I. This reaction is carried out conveniently by mixing said reactants, preferably in a molar ratio of 1:1 and preferably with stirring, either in the absence or presence of a suitable inert solvent, preferably a lower-alkanol, e.g., ethanol. The reaction can be run at higher temperatures, for example up to about 150° C. but to no particular advantage, and can be run using other suitable inert solvents such as benzene, toluene, xylene, chlorobenzene, dimethylformamide, dimethylacetamide, tetramethylurea, pyridine, α-picoline, β-picoline, and the like. Alternatively the above reaction can be carried out by preparing the cyclic isopropylidenyl ethoxymethylenemalonate (II) in situ without its actual isolation by heating a mixture of equal molar quantities of N-(lower-alkyl)-3-PY-aniline, a tri-(lower-alkyl) orthoformate, preferably the triethyl ester, and a cyclic alkylidenyl malonic ester under the reaction conditions discussed above.

The above cyclic alkylidenyl malonic esters and cyclic alkylidenyl ethoxymethylenemalonates referred to above are generally known compounds prepared by conventional methods [Bihlmayer et al., Monatshefte für Chemie 98, 564–578 (1967); Lesher et al. U.S. Pat. No. 3,563,981, issued Feb. 16, 1971 and referred to hereinabove].

The conversion of cyclic alkylidenyl N-(lower-alkyl)-3-PY-anilinomethylenemalonate (I) by heating with polyphosphoric acid to produce 1-(lower-alkyl)-1,4-dihydro-4-oxo-7-PY-3-quinolinecarboxylic acid is carried out by heating the reactants at about 100°–150° C., preferably about 115°–135° C.

The reduction of N-(3-PY-phenyl)-lower-alkanamide (IV, Q = lower-alkanoyl) to produce the corresponding N-(lower-alkyl)-3-PY-aniline (IV, Q = lower-alkyl) was conveniently and preferably carried out using diborane as the reducing agent and was accomplished by mixing the reactants, preferably in a solution in an inert non-polar solvent at about 0° to 75° C. until the reaction is completed. In practicing the invention it was convenient to use tetrahydrofuran as the solvent and to mix the reactants at room temperature, preferably under an inert atmosphere, e.g., nitrogen, and then to reflux the reaction mixture until completion of the reaction. Other inert non-polar solvents can be used, e.g., benzene, toluene, n-hexane, methylene dichloride, and the like. Alternatively, diborane precursors, e.g., diborane-dimethyl sulfide complex, can be used in place of diborane. Also other reducing agents can be used, e.g., lithium aluminum hydride, and the like.

The above-noted intermediate N-(3-PY-phenyl)-(lower-alkanamides) are prepared by reacting the known 3-PY-anilines with a lower-alkanoylating agent, for example, a lower-alkanoyl halide, preferably chloride, a lower-alkanoic anhydride, a lower-alkanoic acid, in particular formic acid for preparation of the formamide, and the like, using conventional acylating procedures. For example, the formamide is prepared by heating a solution of the 3-PY-aniline and 98% formic acid in an inert solvent, e.g., toluene, under reflux using a condenser and a water separator connected to the reaction vessel to separate the water formed by the reaction; the acetamides are preferably prepared by reacting the 3-PY-aniline with either acetic anhydride or with acetyl chloride in the presence of an acid-acceptor.

A. N-(3-PY-PHENYL)-(LOWER-ALKANAMIDES)

A-1. N-[3-(4-Pyridinyl)phenyl]acetamide

A mixture containing 160 g. of 3-(4-pyridinyl)aniline and 250 ml. of acetic anhydride was heated with stirring on a steam bath for one hour after the initial exothermic reaction on mixing the reactants had subsided. The reaction mixture was poured into a mixture of ice and water and the mixture was made basic with 35% aqueous sodium hydroxide solution. The resulting precipitate was collected and washed thoroughly with water. The solid was then recrystallized from 600 ml. of absolute ethanol to yield 116.5 g. of N-[3-(4-pyridinyl)-phenyl]acetamide, m.p. 170°–172° C.

Following the procedure described in Example A-1 but using in place of 3-(4-pyridinyl)aniline a molar equivalent quantity of the appropriate 3-PY-aniline, the N-(3-PY-phenyl)acetamides of Examples A-2 thru A-8 are obtained.

A-2. N-[3-(3-Pyridinyl)phenyl]acetamide using 3-(3-pyridinyl)aniline.

A-3. N-[3-(2-Methyl-4-pyridinyl)phenyl]acetamide using 3-(2-methyl-4-pyridinyl)aniline.

A-4. N-[3-(2-Methyl-5-pyridinyl)phenyl]acetamide using 3-(2-methyl-5-pyridinyl)aniline.

A-5. N-[3-(2,6-Dimethyl-4-pyridinyl)phenyl]acetamide, m.p. 182°–183° C., using 3-(2,6-dimethyl-4-pyridinyl)aniline.

A-6. N-[3-(2,6-Diethyl-4-pyridinyl)phenyl]acetamide using 3-(2,6-diethyl-4-pyridinyl)aniline.

A-7. N-[3-(2-Ethyl-4-pyridinyl)phenyl]acetamide using 3-(2-ethyl-4-pyridinyl)aniline.

A-8. N-[3-(2,3-Dimethyl-4-pyridinyl)phenyl]acetamide using 3-(2,3-dimethyl-4-pyridinyl)aniline.

Following the procedure described in Example A-1 but using in place of acetic anhydride a molar equivalent quantity of the appropriate lower-alkanoic acid anhydride, the N-(3-PY-phenyl)-(lower-alkanamides) of Examples A-9 thru A-12 are obtained.

A-9. N-[3-(4-Pyridinyl)phenyl]-n-propanamide using n-propanoic acid anhydride.

A-10. N-[3-(4-Pyridinyl)phenyl]-N-butanamide using n-butanoic acid anhydride.

A-11. N-[3-(4-Pyridinyl)phenyl]-2-methylpropanamide using 2-methylpropanoic acid anhydride.

A-12. N-[3-(4-Pyridinyl)phenyl]-n-hexanamide using n-hexanoic acid anhydride.

A-13. N-[3-(4-Pyridinyl)phenyl]formamide is obtained by refluxing a solution containing 3-(4-pyridinyl)aniline and a slight molar excess of 98% formic acid in toluene under a condenser with a water separator connected thereto to remove the water formed by the reaction. The reaction mixture is refluxed until no more water separates; the toluene and excess formic acid are distilled-off; and, there remains the desired N-[3-(4-pyridinyl)phenyl]formamide.

B. N-(LOWER-ALKYL)-3-PY-ANILINES

B-1. N-Ethyl-3-(4-pyridinyl)aniline

To a stirred slurry containing 100 g. of N-[3-(4-pyridinyl)phenyl]acetamide and 1200 ml. of tetrahydrofuran at about room temperature (25°–30° C.) was added 1000 ml. of one molar diborane solution in tetrahydrofuran (under nitrogen). After about 700 ml. of the diborane solution had been added, the reaction mixture had become a clear, pale yellow solution. A slightly exothermic reaction was noted during the addition. The reaction mixture was refluxed for five hours and then cooled to room temperature. To the reaction mixture was added 6N hydrochloric acid (300 ml.), mostly near reflux because of an exothermic reaction. The tetrahydrofuran solvent was next distilled-off at atmospheric pressure by heating the mixture on a steam bath. The remaining pale yellow acidic mixture containing some crystals was made basic with 35% aqueous sodium hydroxide solution. The oily layer of the two-phase system was taken up in ether. The ether extract was washed successively with water and saturated brine, dried over anhydrous sodium sulfate and the ether distilled-off in vacuo to yield 103 g. of a yellow solid. This yellow solid was recrystallized from ethyl acetate (about 250 ml.) and dried at room temperature to yield 58 g. of N-ethyl-3-(4-pyridinyl)aniline, m.p. 94°–96° C.

Following the procedure described in Example B-1 but using in place of N-[3-(4-pyridinyl)phenyl]acetamide a molar equivalent quantity of the appropriate N-(3-PY-phenyl)-acetamide, the N-ethyl-3-PY-anilines of Examples B-2 thru B-8 are obtained.

B-2. N-Ethyl-3-(3-pyridinyl)aniline using N-[3-(3-pyridinyl)phenyl]acetamide.

B-3. N-Ethyl-3-(2-methyl-4-pyridinyl)aniline using N-[3-(2-methyl-4-pyridinyl)phenyl]acetamide.

B-4. N-Ethyl-3-(2-methyl-5-pyridinyl)aniline using N-[3-(2-methyl-5-pyridinyl)phenyl]acetamide.

B-5. N-Ethyl-3-(2,6-dimethyl-4-pyridinyl)aniline using N-[3-(2,6-dimethyl-4-pyridinyl)phenyl]acetamide.

B-6. N-Ethyl-3-(2,6-diethyl-4-pyridinyl)aniline using N-[3-(2,6-diethyl-4-pyridinyl)phenyl]acetamide.

B-7. N-Ethyl-3-(2ethyl-4-pyridinyl)aniline using N-[3-(2-ethyl-4-pyridinyl)phenyl]acetamide.

B-8. N-ethyl-3-(2,3-dimethyl-4-pyridinyl)aniline using N-[3-(2,3-dimethyl-4-pyridinyl)phenyl]acetamide.

Following the procedure described in Example B-1 but using in place of N-[3-(4-pyridinyl)phenyl]acetamide a molar equivalent quantity of the appropriate N-[3-(4-pyridinyl)-phenyl]-(lower-alkanamide), the N-(lower-alkyl)-3-(4-pyridinyl)-anilines of Examples B-9 thru B-13 are obtained.

B-9. N-n-Propyl-3-(4-pyridinyl)aniline using N-[3-(4-pyridinyl)phenyl]-n-propanamide.

B-10. N-n-Butyl-3-(4-pyridinyl)aniline using N-[3-(4-pyridinyl)phenyl]-n-butanamide.

B-11. N-Isobutyl-3-(4-pyridinyl)aniline using N-[3-(4-pyridinyl)phenyl]-2-methylpropanamide.

B-12. N-n-Hexyl-3-(4-pyridinyl)aniline using N-[3-(4-pyridinyl)phenyl]-n-hexanamide.

B-13. N-Methyl-3-(4-pyridinyl)aniline using N-[3-(4-pyridinyl)phenyl]formamide.

C. CYCLIC ALKYLIDENYL N-(LOWER-ALKYL)-N-3-PY-ANILINOMETHYLENEMALONATES

C-1. Cyclic isopropylidenyl N-ethyl-3(4-pyridinyl)-anilinomethylenemalonate

A mixture containing 38.8 g. of N-ethyl-3-(4-pyridinyl)aniline, 36.5 g. of cyclic isopropylidenyl ethoxymethylenemalonate and 250 ml. of absolute ethanol was stirred at room temperature whereupon a precipitate started to separate after about 1 hour. The reaction mixture was stirred at room temperature overnight (about 15 hours) and then chilled in an ice bath. The solid was collected, washed with cold ethanol, air-dried and recrystallized from about 300 ml. of ethanol. The recrystallized material was washed successively with cold ethanol and cold ethyl acetate and then air-dried. The dried material was recrystallized from about 250 ml. of ethyl acetate, washed several times with cold ethyl acetate and dried in vacuo at 60° C. for 3 hours to yield 27 g. of cyclic isopropylidenyl N-ethyl-3-(4-pyridinyl)anilinomethylenemalonate, m.p. 131°–133° C.

Following the procedure described in Example C-1 but using in place of N-ethyl-3-(4-pyridinyl)aniline a molar equivalent quantity of the appropriate N-ethyl-3-PY-aniline, the cyclic isopropylidenyl N-ethyl-3-(PY)-anilinomethylene-malonates of Examples C-2 thru C-8 are obtained.

C-2. Cyclic isopropylidenyl N-ethyl-3(3-pyridinyl)-anilinomethylenemalonate using N-ethyl-3-(3-pyridinyl)aniline.

C-3. Cyclic isopropylidenyl N-ethyl-3-(2-methyl-4-pyridinyl)anilinomethylenemalonate using N-ethyl-3-(2-methyl-4-pyridinyl)aniline.

C-4. Cyclic isopropylidenyl N-ethyl-3-(2-methyl-5-pyridinyl)anilinomethylenemalonate using N-ethyl-3-(2-methyl-5-pyridinyl)aniline.

C-5. Cyclic isopropylidenyl N-ethyl-3-(2,6-dimethyl-4-pyridinyl)anilinomethylenemalonate using N-ethyl-3-(2,6-dimethyl-4-pyridinyl)aniline.

C-6. Cyclic isopropylidenyl N-ethyl-3-(2,6-diethyl-4-pyridinyl)anilinomethylenemalonate using N-ethyl-3-(2,6-diethyl-4-pyridinyl)aniline.

C-7. Cyclic isopropylidenyl N-ethyl-3-(2-ethyl-4-pyridinyl)anilinomethylenemalonate using N-ethyl-3-(2-ethyl-4-pyridinyl)aniline.

C-8. Cyclic isopropylidenyl N-ethyl-3-(2,3-dimethyl-4-pyridinyl)anilinomethylenemalonate using N-ethyl-3-(2,3-dimethyl-4-pyridinyl)aniline.

Following the procedure described in Example C-1 but using in place of N-ethyl-3-(4-pyridinyl)aniline a molar equivalent quantity of the appropriate N-(lower-alkyl)-3-(4-pyridinyl)aniline, the cyclic isopropylidenyl N-(lower-alkyl)-3-(4-pyridinyl)anilinomethylenemalonates of Examples C-9 thru C-13 are obtained.

C-9. Cyclic isopropylidenyl N-n-propyl-3-(4-pyridinyl)anilinomethylenemalonate using N-n-propyl-3-(4-pyridinyl)aniline.

C-10. Cyclic isopropylidenyl N-n-butyl-3-(4-pyridinyl)anilinomethylenemalonate using N-n-butyl-3-(4-pyridinyl)aniline.

C-11. Cyclic isopropylidenyl N-isobutyl-3-(4-pyridinyl)anilinomethylenemalonate using N-isobutyl-3-(4-pyridinyl)aniline.

C-12. Cyclic isopropylidenyl N-n-hexyl-3-(4-pyridinyl)anilinomethylenemalonate using N-n-hexyl-3-(4-pyridinyl)aniline.

C-13. Cyclic isopropylidenyl N-methyl-3-(4-pyridinyl)anilinomethylenemalonate using N-methyl-3-(4-pyridinyl)aniline.

D.
1-(LOWER-ALKYL)-1,4-DIHYDRO-4-OXO-7-PY-3-QUINOLINECARBOXYLIC ACIDS

D-1. 1-Ethyl-1,4-dihydro-4-oxo-7-(4-pyridinyl)-3-quinolinecarboxylic acid

A 60 g. portion of polyphosphoric acid was heated to 125° C. and to it was added with stirring 6 g. of cyclic isopropylidenyl N-ethyl-3-(4-pyridinyl)-anilinomethylenemalonate whereupon there was some foaming and the reaction temperature rose to 137° C. The reaction mixture was then heated at about 125° C. for thirty minutes and poured into 350 ml. of water. A small quantity (about 200 mg.) of a brown flocculent solid was filtered-off and the filtrate was made basic with 35% aqueous sodium hydroxide solution. A brown gum was removed by filtering the alkaline mixture through infusorial earth. The clear filtrate was brought to a pH of 5.0 by the addition of 6N hydrochloric acid whereupon a crystalline solid separated. The solid was collected, washed with water, recrystallized from about 30 ml. of hot dimethylformamide, washed with dimethylformamide containing ether and air-dried to yield 850 mg. of 1-ethyl-1,4-dihydro-4-oxo-7-(4-pyridinyl)-3-quinolinecarboxylic acid, m.p. 285°–286.5° C. A mixed melting point with a reference sample of this known compound prepared by a different method showed no depression.

Following the procedure described in Example D-1 but using in place of cyclic isopropylidenyl N-ethyl-3-(4-pyridinyl)anilinomethylenemalonate a molar equivalent quantity of the appropriate cyclic isopropylidenyl N-ethyl-3-(PY)anilinomethylenemalonate, the 1-ethyl-1,4-dihydro-4-oxo-7(PY)-3-quinolinecarboxylic acids of Examples D-2 thru D-8 are obtained.

D-2. 1-Ethyl-1,4-dihydro-4-oxo-7-(3-pyridinyl)-3-quinolinecarboxylic acid using cyclic isopropylidenyl N-ethyl-3-(3-pyridinyl)anilinomethylenemalonate.

D-3. 1-Ethyl-1,4-dihydro-4-oxo-7-(2-methyl-4-pyridinyl)-3-quinolinecarboxylic acid using cyclic isopropylidenyl N-ethyl-3-(2-methyl-4-pyridinyl)anilinomethylenemalonate.

D-4. 1-Ethyl-1,4dihydro-4-oxo-7-(2-methyl-5-pyridinyl)-3-quinolinecarboxylic acid using cyclic isopropylidenyl N-ethyl-3-(2-methyl-5-pyridinyl)anilinomethylenemalonate.

D-5. 1-Ethyl-1,4-dihydro-4-oxo-7-(2,6-dimethyl-4-pyridinyl)-3-quinolinecarboxylic acid using cyclic isopropylidenyl N-ethyl-3-(2,6-dimethyl-4-pyridinyl)anilinomethylenemalonate.

D-6. 1-Ethyl-1,4-dihydro-4-oxo-7-(2,6-diethyl-4-pyridinyl)-3-quinolinecarboxylic acid using cyclic isopropylidenyl N-ethyl-3-(2,6-diethyl-4-pyridinyl)anilinomethylenemalonate.

D-7. 1-Ethyl-1,4-dihydro-4-oxo-7-(2-ethyl-4-pyridinyl)-3-quinolinecarboxylic acid using cyclic isopropylidenyl N-ethyl-3-(2-ethyl-4-pyridinyl)anilinomethylenemalonate.

D-8. 1-Ethyl-1,4-dihydro-4-oxo-7-(2,3-dimethyl-4-pyridinyl)-3-quinolinecarboxylic acid using cyclic isopropylidenyl N-ethyl-3-(2,3-dimethyl-4-pyridinyl)anilinomethylenemalonate.

Following the procedure described in Example D-1 but using in place of cyclic isopropylidenyl N-ethyl-3-(4-pyridinyl)anilinomethylenemalonate a molar equivalent quantity of the appropriate cyclic isopropylidenyl N-(lower-alkyl)-3-(4-pyridinyl)anilinomethylenemalonate, the 1-(lower-alkyl)-1,4-dihydro-4-oxo-7-(4-pyridinyl)-3-quinolinecarboxylic acids of Examples D-9 thru D-13 are obtained.

D-9. 1,4-Dihydro-4-oxo-1-n-propyl-7-(4-pyridinyl)-3-quinolinecarboxylic acid using cyclic isopropylidenyl N-n-propyl-3-(4-pyridinyl)anilinomethylenemalonate.

D-10. 1-n-Butyl-1,4-dihydro-4oxo-7-(4-pyridinyl)-3-quinolinecarboxylic acid using cyclic isopropylidenyl N-n-butyl-3-(4-pyridinyl)anilinomethylenemalonate.

D-11. 1,4-Dihydro-1-isobutyl-4oxo-7-(4-pyridinyl)-3-quinolinecarboxylic acid using cyclic isopropylidenyl N-isobutyl-3-(4-pyridinyl)anilinomethylenemalonate.

D-12. 1-n-Hexyl-1,4-dihydro-4-oxo-7-(4-pyridinyl)-3-quinolinecarboxylic acid using cyclic isopropylidenyl N-n-hexyl-3-(4-pyridinyl)anilinomethylenemalonate.

D-13. 1,4-Dihydro-1-methyl-4-oxo-7-(4-pyridinyl)-3-quinolinecarboxylic acid using cyclic isopropylidenyl N-methyl-3-(4-pyridinyl)anilinomethylenemalonate.

I claim:
1. Cyclic alkylidenyl N-(lower-alkyl)-3-PY-anilinomethylenemalonate having the formula

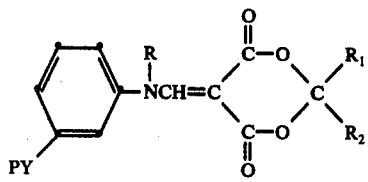

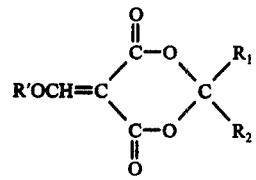

where PY is 4- or 3-pyridinyl or 4- or 3-pyridinyl having one or two lower-alkyl substituents, R is lower-alkyl, and $R_1$ and $R_2$ are each lower-alkyl.

2. Cyclic isopropylidenyl N-ethyl-3-(4-pyridinyl)-anilinomethylenemalonate according to claim 1.

3. The process for preparing a compound according to claim 1 which comprises reacting cyclic alkylidenyl (lower-alkoxy)methylenemalonate having the formula with N-(lower-alkyl)-3-PY-aniline where $R_1$, $R_2$ and PY each has the meaning given in claim 1 and R' is lower-alkyl.

4. The process according to claim 3 which comprises reacting cyclic isopropylidene ethoxymethylenemalonate with N-ethyl-3-(4-pyridinyl)aniline to produce cyclic isopropylidenyl N-ethyl-3-(4-pyridinyl)anilinomethylenemalonate.

* * * * *